(12) United States Patent
Gallant et al.

(10) Patent No.: US 8,051,540 B2
(45) Date of Patent: Nov. 8, 2011

(54) RELEASABLE FASTENING ARRANGEMENT

(75) Inventors: Christopher M. Gallant, Nottingham, NH (US); Mark A. Clarner, Concord, NH (US); Derrick Slowikowski, Merrimack, NH (US); Jefferson Davis, Antrim, NH (US); Wallace L. Kurtz, Jr., Lunenburg, MA (US)

(73) Assignee: Velcro Industries B.V., Curacao ( * ) Notice: Subject to any disclaimer, the term of this patent is extended or adjusted under 35 U.S.C. 154(b) by 923 days.

(21) Appl. No.: 12/040,540

(22) Filed: Feb. 29, 2008

(65) Prior Publication Data
US 2009/0217492 A1    Sep. 3, 2009

(51) Int. Cl.
*A44B 18/00* (2006.01)
*B65D 33/16* (2006.01)

(52) U.S. Cl. ........ 24/306; 24/445; 24/450; 24/452; 24/442; 24/30.5 R; 428/100; 383/42

(58) Field of Classification Search ............ 24/442, 24/306, 445–447, 449–452, 30.5 R; 428/100; 383/42
See application file for complete search history.

(56) References Cited

U.S. PATENT DOCUMENTS

| | | | | |
|---|---|---|---|---|
| 3,462,805 | A * | 8/1969 | Quisling | 24/586.11 |
| 3,899,803 | A * | 8/1975 | Brumlik | 24/444 |
| 4,887,339 | A * | 12/1989 | Bellanger | 24/589.1 |
| 5,802,676 | A * | 9/1998 | Tolan | 24/16 R |
| 6,085,394 | A * | 7/2000 | Hartman | 24/16 PB |
| 6,202,260 | B1 | 3/2001 | Clune et al. | |
| 6,235,369 | B1 * | 5/2001 | Shepard et al. | 428/85 |
| 6,656,403 | B1 | 12/2003 | Clune et al. | |
| 6,775,896 | B2 * | 8/2004 | Dudek et al. | 29/417 |
| 6,991,375 | B2 | 1/2006 | Clune et al. | |
| 7,056,462 | B2 | 6/2006 | Provost et al. | |
| 7,141,283 | B2 | 11/2006 | Janzen et al. | |
| 7,186,025 | B2 | 3/2007 | Shepard et al. | |
| 7,384,415 | B2 | 6/2008 | Kline et al. | |
| 7,478,460 | B2 | 1/2009 | Gallant et al. | |

(Continued)

FOREIGN PATENT DOCUMENTS
WO    WO0008992 A1    2/2000
(Continued)

OTHER PUBLICATIONS

Notification Concerning Transmittal of the International Preliminary Report on Patentability (1 page) and International Preliminary Report on Patentability (6 pages) for International Application No. PCT/US2009/035675, mailed Mar. 18, 2010.

*Primary Examiner* — Robert Sandy
(74) *Attorney, Agent, or Firm* — Fish & Richardson P.C.

(57) ABSTRACT

The present disclosure provides embodiments of a releasable fastening arrangement that can include a first fastening strip secured to and extending over a substrate surface and having a first surface carrying first fastening elements extending from the surface. The releasable fastening arrangement can also include a second fastening strip having a second surface carrying second fastening elements that are engageable by the first fastening elements to form a releasable fastening. The first surface can include a flexible flap that is formed therein, and that is surrounded by other portions of the first surface. The flap can carry at least one of the first fastening elements, and can flap have a distal edge that is displaceable from the substrate surface under peel loads applied to the at least one first fastening element carried by the flap.

20 Claims, 10 Drawing Sheets

U.S. PATENT DOCUMENTS

| | | |
|---|---|---|
| 2003/0031386 A1 | 2/2003 | Shepard et al. |
| 2003/0130644 A1 | 7/2003 | Baker |
| 2004/0008908 A1 | 1/2004 | Shepard et al. |
| 2004/0121694 A1 | 6/2004 | Shepard et al. |
| 2004/0158224 A1 | 8/2004 | Kline et al. |

FOREIGN PATENT DOCUMENTS

| | | |
|---|---|---|
| WO | WO0027721 A9 | 11/2000 |
| WO | WO2004058584 A2 | 7/2004 |

* cited by examiner

FIG. 26

RELEASABLE FASTENING ARRANGEMENT

TECHNICAL FIELD

The present disclosure relates to releasable fastening arrangements, and more particularly to an improved, releasable fastening arrangement having anti-peel properties and increased fastening strength.

BACKGROUND

Releasable fastening arrangements have been implemented to provide releasable couplings in numerous applications. Such fastenings typically include a pair of strip-like fastening members that are releasably engaged with one another. In one instance, an exemplar fastening arrangement can include a hook and loop type fastening arrangement where one fastening member includes a plurality of closely-spaced upstanding fastening projections, such as hook-shaped fastening projections. The fastening projections are used in many different applications for providing both releasable and semi-permanent connection of associated elements. Another fastening member includes a plurality of woven, or non-woven loop fastening elements. The hook-type fastening projections are typically configured for co-action with the loop-type fastening elements to provide a desired connecting or gripping action.

Depending upon the configuration of the multi-hook fastener member, many different types of materials and fabrics are adapted for co-action therewith to effect joining of the associated structures. Not only do such fastening devices have many applications for wearing apparel, recreational equipment, covers for cars and boats, and the like, such devices can be advantageously employed in other applications. Such applications take advantage of the convenient engaging and disengaging action that promotes joining of associated structures in a selectively releasable manner. For example, such fastening arrangements are finding ever-increasing use in the automotive industry for efficient fabrication and assembly of components such as seats, interior trim, and the like.

Releasable fastening arrangements can include at least two engagement strength characteristics. One characteristic includes a peel strength, and another characteristic includes a shear strength. Peel strength corresponds to the force required to disengage the fastening members from one another, by peeling one fastening member upward, and away from the other fastening member. Shear strength corresponds to the force required to disengage the fastening members from one another, by pulling at least one of the fastening members away from the other in a plane that is parallel to the fastening members. Typically, the engagement strength of the fastening members is higher in the shear direction than in the peel direction. In some instances, peeling of one fastening member can inadvertently occur, and can result in an undesired disengagement of the fastening members.

SUMMARY

As discussed in detail herein, embodiments of the fastening arrangement of the present disclosure improves upon previously existing hook and loop fastening arrangements. More particularly, embodiments of the fastening arrangement of the present disclosure provide improved anti-peel properties and increased fastening strength. As a result, inadvertent, or otherwise undesired disengagement of the fastening arrangement can be inhibited.

One aspect of the present disclosure features a releasable fastening arrangement that includes a first fastening strip secured to and extending over a substrate surface and having a first surface carrying first fastening elements that extend therefrom. The releasable fastening arrangement also includes a second fastening strip having a second surface carrying second fastening elements that are engageable by the first fastening elements to form a releasable fastening. The first surface includes a flexible flap that is formed therein, and that is surrounded by other portions of the first surface. The flap carries at least one of the first fastening elements, and has a distal edge that is displaceable from the substrate surface under peel loads applied to at least one first fastening element carried by the flap.

In some examples, the flap is defined by a slit extending through the first fastener strip, such that the flap comprises a portion of the first surface extending from a remainder of the first surface only along one side of the flap opposite the distal edge. The slit can be curved.

In another example, the flap is arcuate and is flexible along a slanted axis.

In another example, the flap extends across a width of the first fastening strip.

In other examples, the releasable fastening arrangement further includes a second flap that is formed in the first surface, and that is surrounded by other portions of the first surface. The second flap carries at least one of the first fastening elements, and has a distal edge that is displaceable from the substrate surface under peel loads applied thereto. The second flap extends across a width of the first fastening strip.

In another example, the first fastening strip includes multiple, spaced apart flaps, each carrying a respective one or more first fastening elements and each surrounded by non-flap portions of the first fastening product.

In other examples, the first fastening elements are provided as an array of fastening projections. The fastening projections include hook-type fastening projections. The first fastening elements and the first surface can be of a single, seamless mass of resin.

In still another example, the second fastening elements are provided as a field of fibers that are releasably engageable by the first fastening elements.

In yet another example, the first fastening strip is secured to the substrate surface in a region directly surrounding the flap.

Another aspect of the present disclosure features a product having a first component, and a second component that releasably engage one another. Embodiments of the product further include a releasable fastening arrangement having a first fastening strip secured to and extending over a substrate surface of the first component and having a first surface carrying first fastening elements extending from the surface. A second fastening strip is secured to and extends over a substrate surface of the second component, and has a second surface carrying second fastening elements that are engageable by the first fastening elements to form a releasable fastening. The first surface includes a flexible flap that is formed therein, and that is surrounded by other portions of the first surface. The flap carries at least one of the first fastening elements, and has a distal edge that is displaceable from the substrate surface under peel loads applied to the at least one first fastening element carried by the flap.

Another aspect of the present disclosure features a method of forming a touch fastener product. The method includes forming from resin a sheet-form base and first fastening elements that extend from a broad surface of the base, and forming slits defining flaps of the base connected only along an adjoining edge but otherwise flexible out of a plane of the base, each flap carrying at least one of the first fastening elements.

In another aspect, forming slits can include slitting the base.

In another aspect, forming slits can include punching the base.

In other aspects, the first fastening elements are provided as an array of projection stems. Methods can further include forming engageable heads on distal ends of the projection stems. In some aspects, forming the heads can include molding the heads integrally with the stems. In some aspects, the heads are formed after the stems are formed. In some aspects, the heads are formed by deforming resin of the stems to form the heads.

Still another aspect of the present disclosure features a releasable touch fastener product that includes a flexible sheet-form base having an exposed surface, and a field of fastening elements extending from the surface. The base is slit to define flaps that have a distal edge, and that are connected only along an adjoining edge, but otherwise flexible out of a plane of the base, each flap carrying at least one of the fastening elements of the field.

In other examples, the flap is defined by a slit extending through the flexible sheet form, such that the flap comprises a portion of the surface extending from a remainder of the surface only along one side of the flap opposite the distal edge. The flap can be arcuate. The flap can extend across a width of the base.

In other examples, the fastening elements can include hook-type fastening projections. The projection and the surface can be of a single, seamless mass of resin.

In other aspects, the present disclosure provides embodiments of a releasable fastening arrangement that includes a first fastening member secured to and extending over a substrate surface and having a surface carrying fastening elements. The surface includes a flexible flap that is formed therein, and that is surrounded by other portions of the surface. The flap carries at least one of the fastening elements, and has a distal edge that is displaceable from the substrate surface under peel loads applied to at least one fastening element carried by the flap.

In another example, the releasable fastening arrangement further includes a second fastening member that is engageable by the first fastening elements to form a releasable fastening.

The various embodiments of the fastening arrangements described herein improve the engagement strength of mating fastening members. Consequently, lighter weight, and/or a reduced amount of fastening elements can be implemented. More specifically, the engagement strength of fastening members is decreased when using lighter weight, and/or a reduced amount of fastening elements. The increased engagement strength associated with the fastening arrangements of the present disclosure can offset any decrease in engagement strength that may result when using lighter weight, and/or a reduced amount of fastening elements. Furthermore, the fastening arrangements described herein, inhibit accidental disengagement of fastening members. This can be particularly beneficial in the case of implementation with a personal care garment, such as a diaper. This can also be beneficial in other applications, such as securing a fabric to a surface, as is the case in mold-in fastening arrangements for seats.

The details of one or more embodiments of the present disclosure are set forth in the accompanying drawings and the description below. Other features, objects, and advantages of the embodiments of the present disclosure will be apparent from the description and drawings, and from the claims.

DESCRIPTION OF DRAWINGS

Like reference symbols in the various drawings indicate like elements.

DETAILED DESCRIPTION

The present disclosure is directed to hook and loop fastening. More specifically, various embodiments of an improved hook and loop fastening arrangement having anti-peel properties, and increased fastening strength are described. As illustrated and described herein, the various embodiments of the hook and loop fastening arrangement of the present disclosure can be implemented with reclosable bags, garments, such as diapers, and/or other applications, such as securing a fabric to a surface. It is anticipated, however, that the various embodiments of the fastening arrangement of the present disclosure can be implemented with any number of products.

Figure 1:
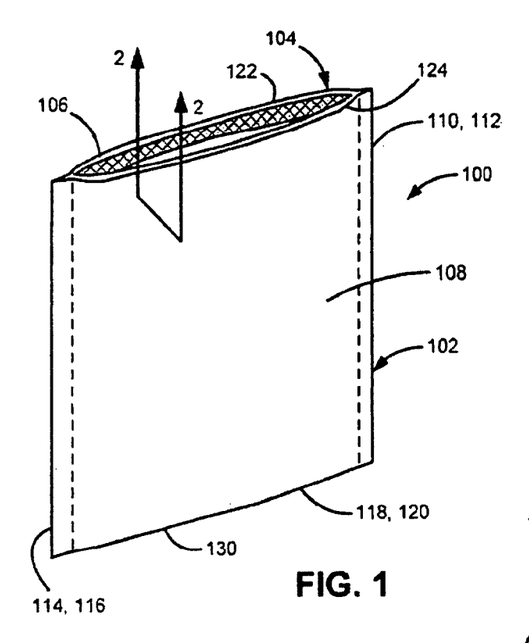
FIG. 1 is a perspective view of an exemplar reclosable bag having a hook and loop fastening arrangement in accordance with the present disclosure.

Referring now to FIG. 1, reclosable bag 100 includes a body 102 and an exemplar fastening arrangement 104. Body 102 includes a first opposing side wall 106 and a second opposing side wall 108, each of which has respective first edges 110, 112, second edges 114, 116, bottom edges 118, 120, and top edges 122, 124. In one embodiment, top edges 122, 124 are not joined together in at least a central portion of side walls 106, 108 and bottom edges 118, 120 are joined at a fold 130 in a single sheet of bag film. This configuration results in an open end of bag 100 opposite to fold 130. However, any suitable arrangement capable of forming a pouch having an open end may be used. For example, bag 100 may be formed from two separate sheets of bag material sealed at selected corresponding edges.

Figure 2:
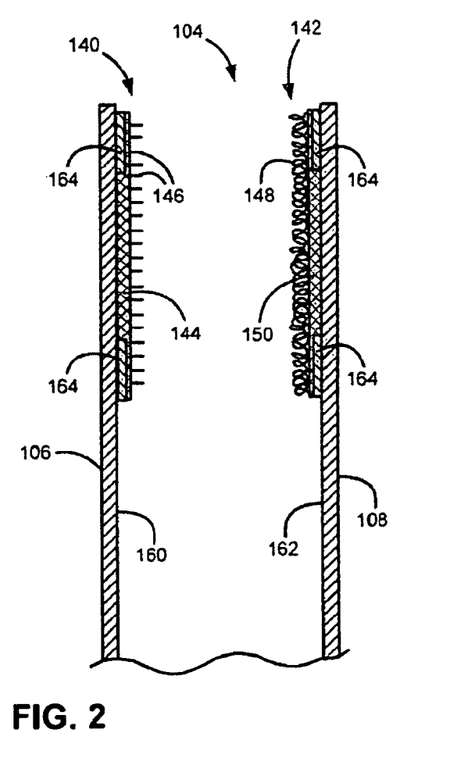
FIG. 2 is a partial cross-sectional view taken along line 2-2 in FIG 1.

As shown in FIG. 2, fastening arrangement 104 includes a hook fastening product, or strip 140 and a loop fastening product, or strip 142. Hook fastening strip 140 includes a fastening base, or substrate 144 and an array of fastener projections 146, such as hook fastener elements, that are integrally molded with and extend from a surface of fastening base 144. Loop fastening strip 142 includes fastening elements that can be provided as a band of non-woven material forming engageable loop fastening elements 148, which are secured to a fastening base, or substrate 150, such as a resin base, for example. Hook and loop fastening strips 140, 142 are arranged such that fastening elements 146, 148 engage one another to hold the fastening strips 140, 142 together. In this manner, the opening of the reclosable bag 100, for example, can be closed. Fastening elements 146 can be J-hook, and/or palm tree type fastening elements having a height between about 0.010 inch and about 0.020 inch (most preferably about 0.015 inch), and fastening elements 148 are of a woven, or non-woven fiber material encapsulated in fastening base 150. Suitable loop materials also include woven and knit loop materials, among other loop materials known in the art.

Hook fastening strip 140 can be attached to an inner surface 160 of side wall 106 and loop fastening strip 142 is attached to an inner surface 162 of side wall 108. In this embodiment, side wall 106 functions as a substrate, to which hook fastening strip 140 is attached, and side wall 108 functions as a substrate, to which loop fastening strip 142 is attached. More particularly, hook and loop fastening strips 140, 142 can be attached to their respective inner surfaces 160, 162 along attachment regions 164, which run along the top and bottom edges of hook and loop fastening strips 140, 142. Attachment regions 164 can include welds, for example. More specifically, methods of attaching the components of fastening arrangement 104 to bag 100 include, but are not limited to, welding (e.g., heat sonic or RF means), gluing, or stitching. One particular method of attaching a fastening component to a bag of a compatible resin is by directly welding the resin of the fastening component substrate to the resin of the bag, as discussed below. In this manner, a polyethylene fastening arrangement, for example, may be readily welded to a polyethylene bag. Preferably, the resin of the fastening arrangement components is compatible with the resin of the bag body, to enable direct welding of the two together. In some cases, the resin of the fastening arrangement components and the bag body are both polyethylene.

Figure 3:
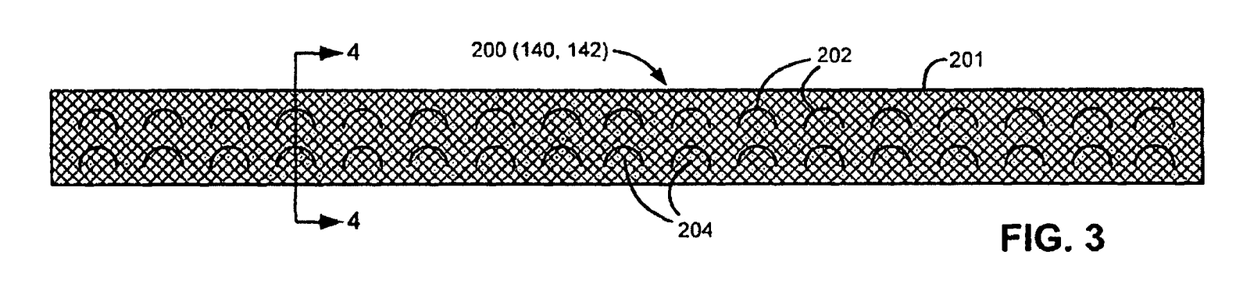
FIG. 3 is a plan view of a fastening strip in accordance with an embodiment of the present disclosure.
Figure 4:
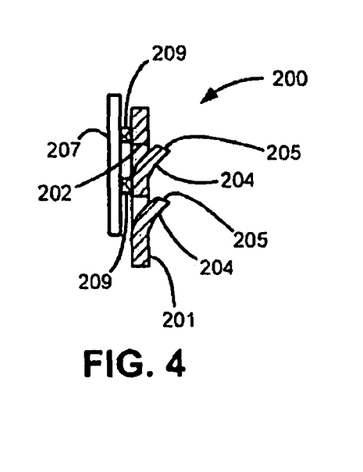
FIG. 4 is a cross-sectional view taken along line 4-4 in FIG. 3.
Figure 5:
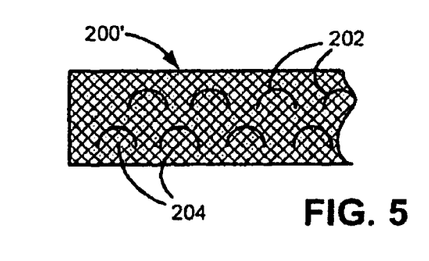
FIG. 5 is a partial plan view of a fastening strip in accordance with other embodiments of the present disclosure.
Figure 6:
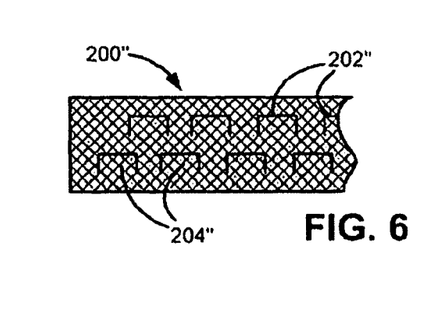
FIG. 6 is a partial plan view of a fastening strip in accordance with other embodiments of the present disclosure.

Referring now to FIGS. 3-6, a fastening arrangement in accordance with the present disclosure will be described in further detail. With particular reference to FIGS. 3 and 4, an exemplar fastening strip 200 including a fastening base or substrate 201 is illustrated. Although fastening elements are not illustrated, fastening strip 200 can include a hook fastening strip, such as hook fastening strip 140, or can include a loop fastening strip, such as loop fastening strip 142. Fastening strip 200 includes a plurality of slits 202 therein, which form a corresponding plurality of flexible flaps 204. Although slits 202, and therefore flaps 204, are arcuate, or semi-circular in shape, slits 202/flaps 204 can include any one of a plurality of shapes, as discussed in further detail below. Further, although fastening strip 200 includes two rows of slits 202/flaps 204 that are aligned with one another, any other arrangement, alignment, or misalignment of slits 202/flaps 204 is within the scope of the present disclosure. As seen in FIG. 5, for example, the rows of slits 202/flaps 204 of fastening strip 200' are misaligned. As also seen in FIG. 5, flaps 204 include a distal edge that is displaceable under peel loads that are applied to at least one fastening element carried by flaps 204, as discussed in further detail below. As another example, FIG. 6 illustrates square-shaped slits 202" and corresponding flaps 204" that are arranged in misaligned rows in fastening strip 200".

In the case of fastening strip 200 including a loop fastening strip of a woven material, the material is secured to substrate 201 such that cutting of the material to form slits 202 and flaps 204 does not result in un-weaving of the material. For example, a binder layer can be applied to bind the woven loop material to substrate 201. Consequently, intermittent cutting of the woven material does not result in the material becoming un-woven, particularly in the area of flaps 204. In the case of fastening strip 200 including a loop fastening strip of non-woven material, the material is also secured to substrate 201 such that cutting of the material does not displace the material from substrate 201.

Referring again to FIG. 4, fastening body, or substrate 201 can be secured to a surface of a substrate 207 in attachment regions 209. In the embodiment of FIG. 4, attachment regions are disposed directly adjacent to, and surround slits 204. In this manner, fastening strip 200 is secured to substrate 207 at or near the area of flaps 204. Furthermore, fastening strip 200 can be secured to substrate 207 in other areas including along the edges of fastening strip 200, as similarly described above with respect to fastening strips 140, 142. In general, the entire back surface of fastening strip 200 can be secured to substrate 207 except in the area of flaps 204.

As explained in detail above, one exemplar method of attaching a fastening strip to a substrate includes directly welding the resin of the fastening strip to the resin of the substrate. In this manner, a polyethylene fastening arrangement, for example, may be readily welded to a polyethylene substrate. Preferably, the resin of the fastening arrangement components is compatible with the resin of the substrate, to enable direct welding of the two together. In some cases, the resin of the fastening arrangement components and the substrate are both polyethylene.

Figure 7A:
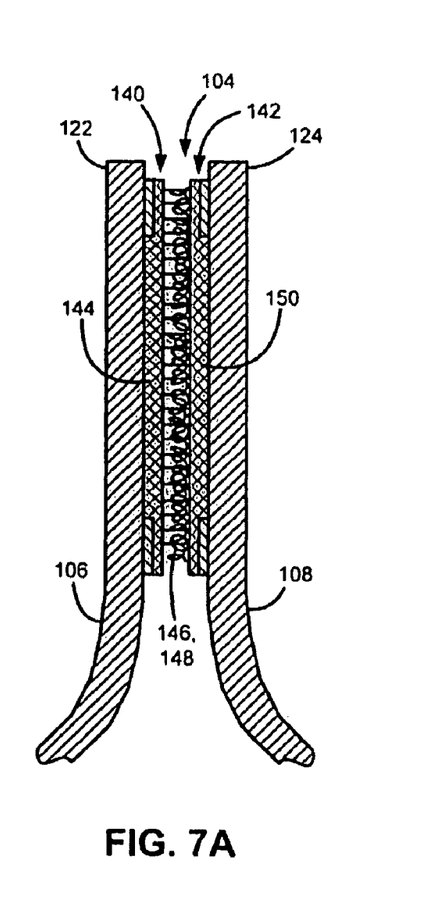
FIGS. 7A-7C are cross-sectional views illustrating a release progression of an embodiment of a fastening arrangement in accordance with the present disclosure.
Figure 7B:
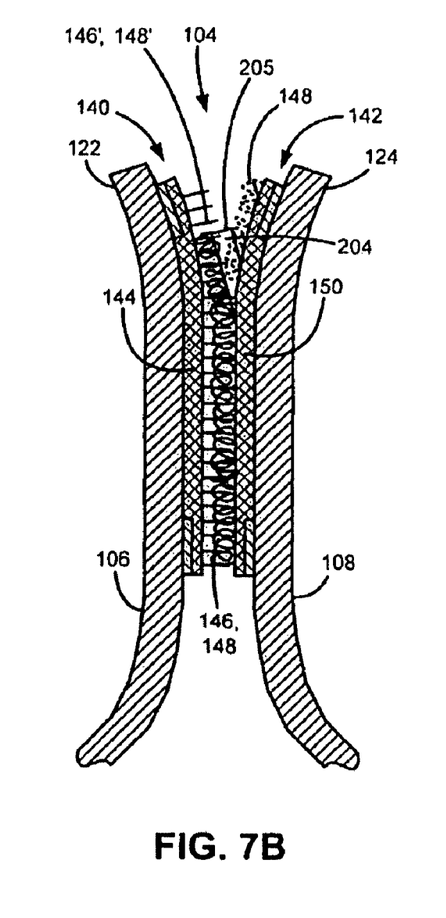
Figure 7C:
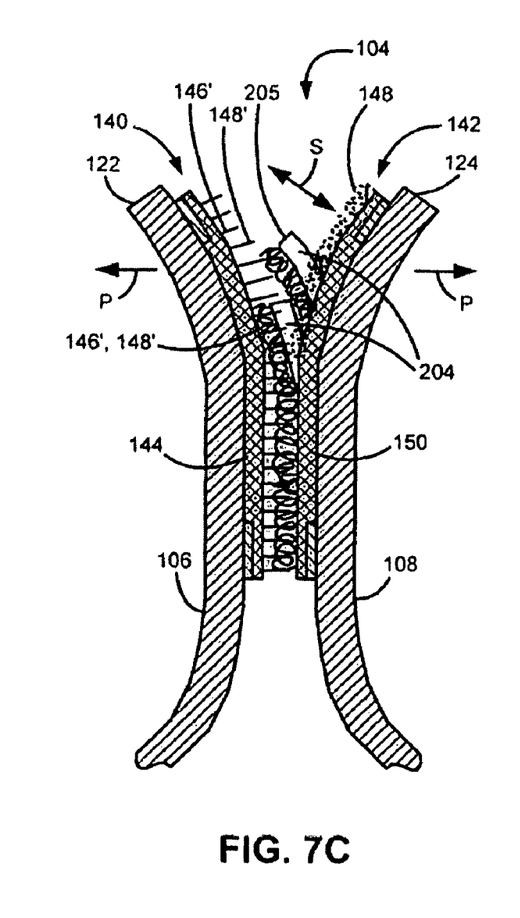

Referring now to FIGS. 7A-7C, a progression of releasing an exemplar fastening arrangement 104 in accordance with the present disclosure will be described in detail. With particular reference to FIG. 7A, hook and loop fastening elements 146, 148 are initially engaged with one another, holding hook and loop fastening strips 140, 142, and thus sidewalls 106, 108 of bag 100, for example, together. With particular reference to FIG. 7B, as top edge 124 of sidewall 108 is pulled, or otherwise peeled away from top edge 122 of sidewall 106, hook and loop fastening elements 146, 148 begin to disengage one another. Loop fastening strip 142, however, is arranged to include slits 202 and flaps 204, as described above with respect to FIGS. 3-6. Accordingly, as top edges 122, 124 are pulled from engagement with one another, portions 146', 148' of hook and loop fastening elements 146, 148, respectively, which are associated with the flap region, maintain engagement with one another. Consequently, flaps 204 are drawn from fastening base 150. More specifically, distal edge 205 of flap 204 is displaced from fastening strip base 150 under peel loads that are applied to it through portion 148' of the fastening elements carried by flap 204.

With particular reference to FIG. 7C, as top edges 122, 124 are pulled further from one another, flap 204 increasingly extends from fastening base 150. More specifically, flap 204 can be drawn out to be past perpendicular and up to approximately 180° relative to fastening base 150. While portions 146, 148 of hook and loop faster elements 146, 148, respectively, disengage under a peel force, indicated by arrow P, portions 146', 148' of hook and loop faster elements 146, 148, respectively, are eventually disengaged using a shear force. In other words, by maintaining engagement of portions 146', 148', flap 204 is drawn from fastening base 150, and the disengagement direction transfers from a pull, or peel direction to a shear direction. The shear direction is indicated by arrow S.

Figure 8A:
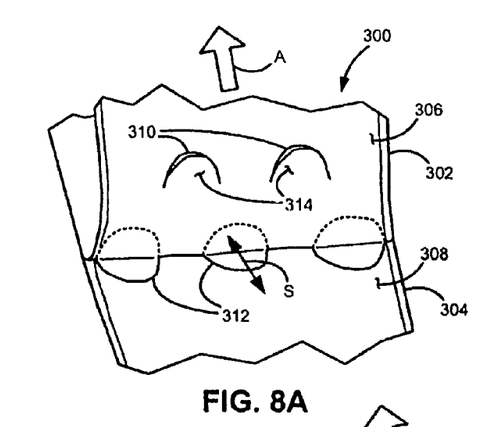
FIGS. 8A and 8B are partial perspective views illustrating a release progression of embodiments of fastening arrangements in accordance with the present disclosure.
Figure 8B:
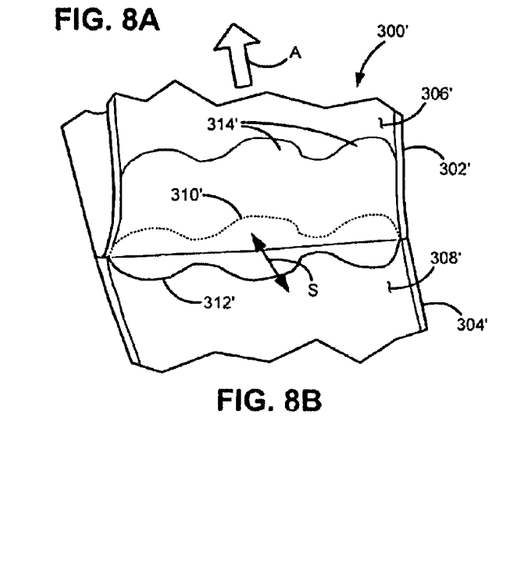

Referring now to FIGS. 8A and 8B, release progressions of exemplar fastening arrangements 300, 300', respectively, in accordance with the present disclosure are illustrated. Fastening arrangement 300 includes a first fastening strip 302, and a second fastening strip 304. First fastening strip 302 can include a region 306 of hook or loop fastening elements (not illustrated). Second fastening strip 304 can include a region 308 of the other hook or loop fastening elements (not illustrated). More specifically, if region 306 includes hook fastening elements, or projections, region 308 includes loop fastening elements, and if region 306 includes loop fastening elements, region 308 includes hook fastening elements, or projections. Fastening strip 302 includes slits 310 that define flaps 312. Sub-regions 314 of fastening elements are associated with flaps 312. As fastening strip 302 is pulled from fastening strip 304 in the direction indicated by arrow A, sub-regions 314 of fastening elements remain engaged with region 308 of fastening strip 304 longer, drawing flaps 312 from fastening strip 302 until they can be past perpendicular and up to approximately 180° relative to fastening strip 302. Consequently, a peel force that is applied to fastening strip 302 to disengage fastening strip 302 from fastening strip 304 becomes a shear force at flaps 312 in the direction indicated by the arrow S.

Fastening arrangement 300' includes a first fastening strip 302', and a second fastening strip 304'. First fastening strip 302' can include a region 306' of hook or loop fastening elements (not illustrated). Second fastening strip 304' can include a region 308' of the other hook or loop fastening elements (not illustrated). More specifically, if region 306' includes hook fastening elements, region 308' includes loop fastening elements, and if region 306' includes loop fastening elements, region 308' includes hook fastening elements, or projections. Fastening strip 302' includes slits 310' that define flaps 312'. Slits 310' run substantially across fastening strip 302' such that flaps 312' also run substantially across fastening strip 302'. Sub-regions 314' of fastening elements are associated with flaps 312'. As fastening strip 302' is pulled from fastening strip 304' in the direction indicated by arrow A, sub-regions 314' of fastening elements remain engaged with region 308' of fastening strip 304' longer, drawing flap 312' from fastening strip 302' until they can be past perpendicular and up to approximately 180° relative to fastening strip 302'. Consequently, a force that is applied to fastening strip 302' to disengage fastening strip 302' from fastening strip 304' becomes a shear force at flap 312' in the direction indicated by the arrow S.

Figure 9:
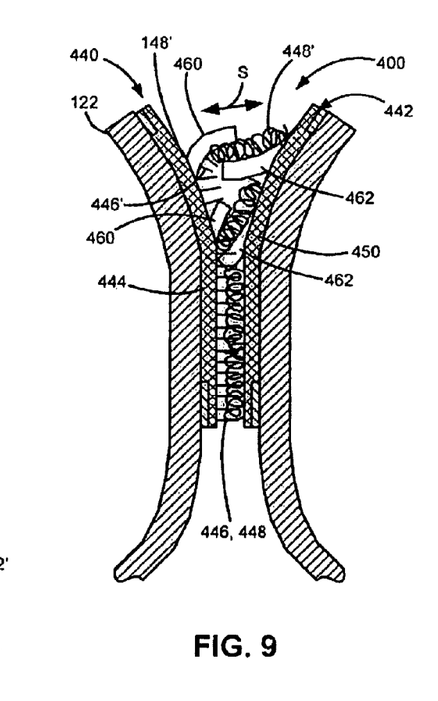
FIG. 9 is a cross-sectional view illustrating a release progression of another embodiment of a fastening arrangement in accordance with the present disclosure.

Referring now to FIG. 9, a release progression of another fastening arrangement 400 in accordance with the present disclosure is illustrated. Fastening arrangement 400 includes a hook fastening strip 440 and a loop fastening strip 442. Hook fastening strip 440 includes a fastening base 444 and an array of hook fastening elements, or projections 446 integrally molded with and extending from fastening base 444. Loop fastening strip 442 includes a band of woven, or non-woven material forming engageable loop fastening elements 448 secured to a fastening base 450, such as a resin base, for example. Hook and loop fastening strips 440, 442 are arranged such that fastening elements 446, 448 engage one another to hold the fastening strips 440, 442 together. Fastening elements 446 can be J-hook and/or palm tree type fastening elements having a height between about 0.010 inch and about 0.020 inch (most preferably about 0.015 inch), and fastening elements 448 are of a non-woven fiber material encapsulated in fastening base 450. Suitable loop materials also include woven and knit loop materials.

As discussed in further detail below, fastening strips 440, 442 each include flaps 460, 462, respectively. Flaps 460, 462 can be oriented approximately 180° relative to one another. When fastening strips 440, 442 are pressed into engagement with one another, at least a portion of flaps 460 align with and engage a corresponding portion of flaps 462. More specifically, a region 446' of hook elements 446 that are associated with flap 460 engage a region 448' of loop elements 448 that are associated with flap 462. As fastening strips 440, 442 are peeled away from one another, hook and loop fastening elements 446, 448 are pulled from engagement with one another. Regions 446', 448' of fastening elements 446, 448, however, remain engaged with one another, drawing flaps 460, 462 from fastening strips 440, 442, respectively. Eventually, flaps 460, 462 can be at or near parallel to one another in a shear direction S, indicated by the arrow. In order for flaps 460, 462 to disengage one another, a sufficient shear force must be provided in the shear direction S.

Figure 10:
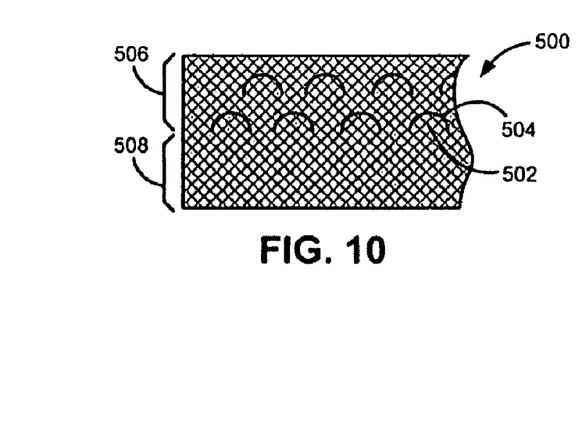
FIGS. 10-18 are respective plan views of other exemplar embodiments of a fastening strip in accordance with the present disclosure.

With particular reference to FIG. 10, a plan view of an exemplar fastening strip 500 is illustrated. Fastening strip 500 can include a hook fastening strip or can include a loop fastening strip, and includes a plurality of slits 502 therein, which form a corresponding plurality of flaps 504. Although slits 502, and therefore flaps 504, are arcuate, in this case semi-circular, in shape, slits 502 and flaps 504 can include any one of a plurality of shapes, as discussed in further detail below. Further, although fastening strip 500 includes two rows of slits 502/flaps 504 that are misaligned, any other arrangement, alignment, or misalignment of slits 502/flaps 504 is within the scope of the present disclosure. Fastening strip includes a first region 506 that is without slits and flaps, and a second region 508, within which slits 502/flaps 504 are located. In this manner, as fastening strip 500 disengages a corresponding, mating fastening strip (not shown), first region 506 is disengaged through application of a peel force, and second region 508 is disengaged through application of a combined peel and shear force, as described in further detail below.

Figure 11:
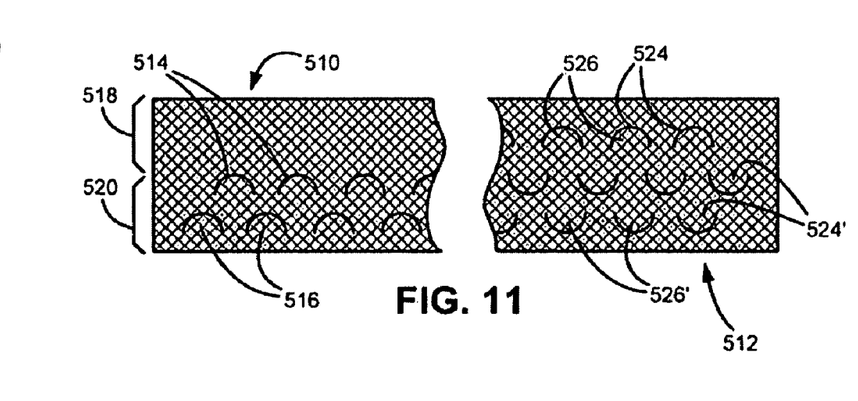
Figure 12:
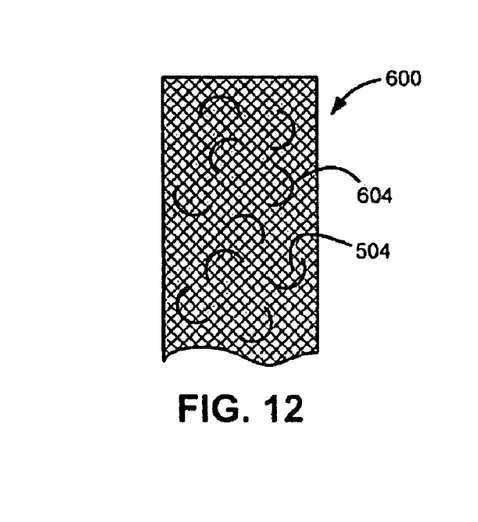
Figure 13:
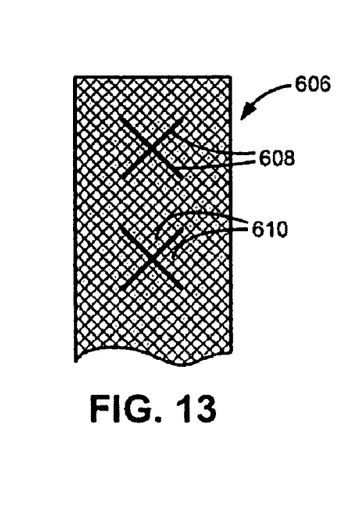
Figure 14:
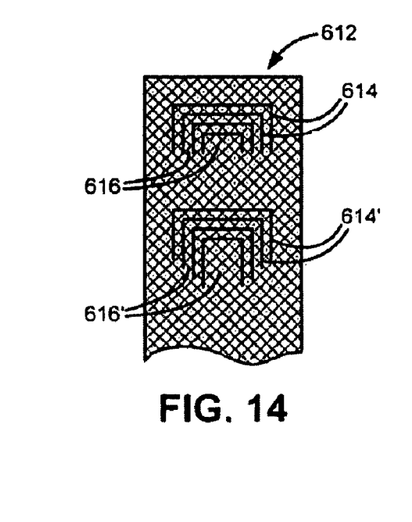

With particular reference to FIG. 11, mating fastening strips 510, 512, respectively, are illustrated. Fastening strip 510 can include a hook fastening strip or can include a loop fastening strip, and includes a plurality of slits 514 therein, which form a corresponding plurality of flaps 516. Although slits 514, and therefore flaps 516, are semi-circular in shape, slits 514 and flaps 516 can include any one of a plurality of shapes, as discussed in further detail below. Further, although fastening strip 510 includes two rows of slits 514/flaps 516 that are misaligned, any other arrangement, alignment, or misalignment of slits 514/flaps 516 is within the scope of the present disclosure. Fastening strip 510 includes a first region 518 that is without slits and flaps, and a second region 520, within which slits 514 and flaps 516 are located.

With continued reference to FIG. 11, fastening strip 512 can include a hook fastening strip or can include a loop fastening strip. For example, if fastening strip 510 is provided as a hook fastening strip, fastening strip 512 is provided as a mating loop fastening strip. In the alternative, if fastening strip 510 is provided as a loop fastening strip, fastening strip 512 is provided as a mating hook fastening strip. Fastening strip 512 includes a first plurality of slits 524 therein, which form a corresponding plurality of flaps 526, and a second plurality of slits 524', which form a corresponding plurality of flaps 526'. Although slits 524, 524', and therefore flaps 526, 526', are semi-circular in shape, slits 524, 524' and flaps 526, 526' can include any one of a plurality of shapes, as discussed in further detail below. Further, although fastening strip 512 includes three rows of slits 524, 524'/flaps 526, 526' that are misaligned, any other arrangement, alignment, or misalignment of slits 524, 524'/flaps 526, 526' is within the scope of the present disclosure. Slits 524, 524'/flaps 526, 526' are disposed along the entire height of fastening strip 512.

When fastening strips 510, 512 engage one another, the fastening elements of first region 518 of fastening strip 510 engage corresponding fastening elements of fastening strip 512 including those associated with flaps 526. The fastening elements of second region 520 of fastening strip 510 engage corresponding fastening elements of fastening strip 512. More specifically, the fastening elements associated with flaps 516 engage the fastening elements associated with flaps 526'. Flaps 516, 526' are oriented approximately 180° relative to one another. As fastening strips 510, 512 initially disengage from one another, a combined pull and shear force resulting from the engagement of flaps 526 with first region 518 is required. This is similar to the progression described above with respect to FIGS. 7A-7C. As the disengagement of fastening strips 510, 512 progresses, the peel force and the added shear force resulting from the engagement of flaps 516 in second region 520 and flaps 526' are required. This is similar to the progression described above with respect to FIG. 9.

Referring now to FIGS. 12-18, various exemplar embodiments of fastening strips in accordance with the present disclosure will be described in further detail. Fastening strips can include a hook fastening strip or can include a loop fastening strip. Fastening strip 600 of FIG. 12 includes a plurality of slits 602 therein, which form a corresponding plurality of flaps 604. Although slits 602, and therefore flaps 604, are semi-circular in shape, slits 602 and flaps 604 can include any one of a plurality of shapes, as discussed in further detail below. The slits 602/flaps 604 are randomly disposed along fastening strip 600 and are oriented in random directions relative to one another. Fastening strip 606 of FIG. 13 includes a plurality of cross, or X-shaped slits 608 that define a plurality of triangular-shaped flaps 610. Fastening strip 612 of FIG. 14 includes a plurality of slits 614, 614' that define flaps 616, 616', respectively. Slits 614 are nested relative to one another, gradually decreasing in size. Consequently, flaps 616 are nested relative to one another, and gradually decrease in size. In an alternative arrangement, slits 614' are nested relative to one another and gradually decrease in size. Slits 614', however, gradually decrease in width and increase in height moving from the outermost slit 614' to the innermost slit 614'. Consequently, flaps 616' are nested relative to one another, and gradually decrease in width and increase in height moving from the outermost flap 616' to the innermost flap 616'. Although the slits 614, 614'/flaps 616, 616' are rectangular in shape, it is appreciated that other shapes can be implemented.

Figure 15:
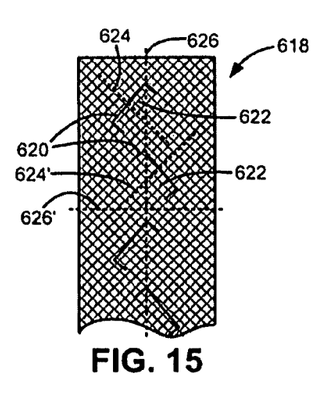
Figure 16:
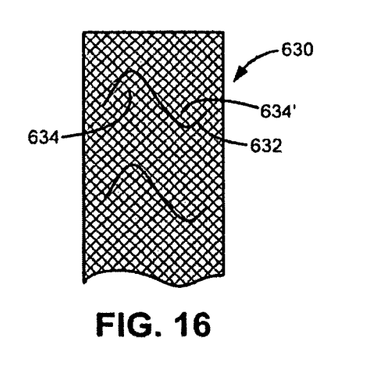
Figure 17:
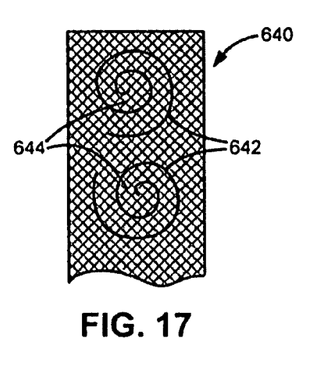
Figure 18:
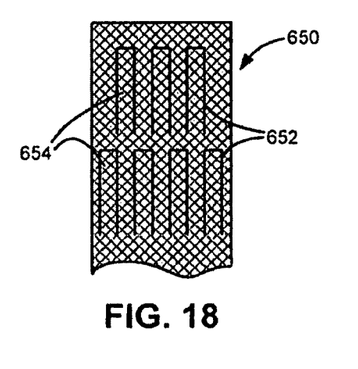

Fastening strip 618 of FIG. 15 includes a plurality of rectangular-shaped slits 620 that define corresponding flaps 622. Slits 620, and thus flaps 622 include directional axes 624, 624', that are arranged to intersect, or otherwise be non-parallel to a directional axes 626, 626' of fastening strip 618. Although slits 620/flaps 622 are rectangular in shape, it is appreciated that other shapes can be implemented. Fastening strip 630 of FIG. 16 includes sinusoidal slits 632 that define opposing flaps 634, 634'. More specifically, one slit 632 defines a flap 634 that is foldable in a first direction, as well as a flap 634' that is foldable in a second direction opposite to the first direction. Fastening strip 640 of FIG. 17 includes spiral-shaped slits 642 that define spiral-shaped flaps 644. Fastening strip 650 of FIG. 18 includes elongated, rectangular-shaped slits 652 that define elongated, rectangular-shaped flaps 654. The length of flaps 654 increases the time, during which flaps 654 are in shear, relative to a shorter flap, for example, when implemented in a fastening arrangement, such as those described herein.

Figure 19:
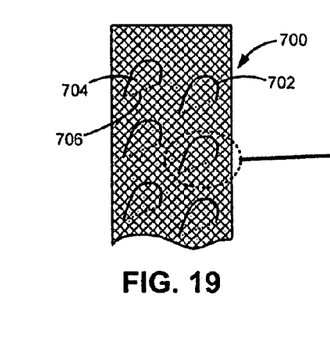
FIG. 19 is a plan view of an exemplar embodiment of a fastening strip in accordance with the present disclosure.
Figure 20:
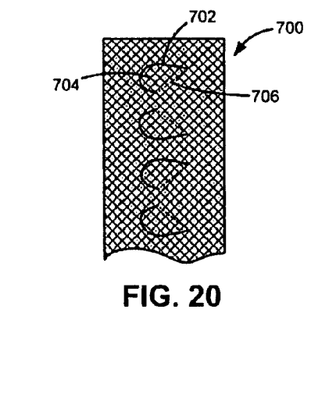
FIG. 20 is a detailed view of a slit of the fastening strip of FIG. 19.
Figures 21A, 21B:
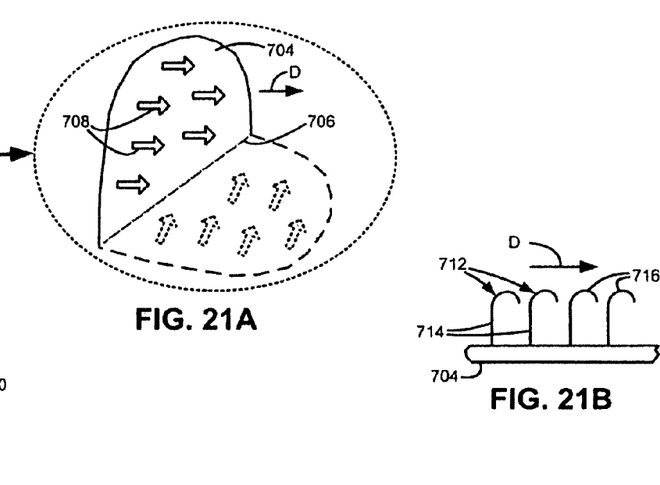
FIG. 21A is a plan view of an exemplar embodiment of a slit of a fastening strip in accordance with the present disclosure.
FIG. 21B is a schematic side view of exemplar hook fasteners.

Referring now to FIGS. 19, 20, and 21A-21B, an alternative arrangement of a fastening strip will be discussed. With particular reference to FIG. 19, a fastening strip 700 includes arcuate slits 702 that define arcuate flaps 704. Consequently, flaps 704 fold along sloped, or slanted axes 706. FIG. 20 illustrates a similar arrangement, where slits 702 and flaps 704 are orientated in a different direction. With particular reference to FIGS. 21A and 21B, arrows 708 indicate an orientation direction of fastening elements of flap 704. For example, if fastening strip 700 includes J-hook fastening elements, or projections, arrows 708 indicate the direction, in which the fastening elements run. More specifically, each fastening element 712 includes a stem portion 714 and a crook portion 716. Crook portions 716 open in a direction D. It is appreciated, however, that fastening elements of fastening strip 700 are not limited to J-hook type fastening elements, and can include other fastening elements known in the art.

In the exemplar case of FIGS. 21A and 21B, fastening elements 712 run in the direction D. As flap 704 is induced to fold along axis 706, flap 704 moves from a first disposition (shown in solid-line) toward a second disposition (shown in phantom). In the second disposition, the fastening elements run in a direction that is non-parallel to the direction D. Although the fastening elements themselves don't move on flap 704, the orientation of the fastening elements relative to the direction D alters. For example, the orientation of the fastening elements rotates approximately 60°-90° relative to the direction D, as flap 704 folds along axis 706 to the orientation shown in phantom. Consequently, as the fastening elements associated with flap 704 disengage from fastening elements of another fastening strip (i.e., a fastening strip that engages fastening strip 700), the orientation of the fastening elements of flap 704 twists, or rotates relative to the fastening elements, from which they are disengaging. Consequently, the fastening elements can become more entangled, and the force required to disengage the fastening elements can be increased. As discussed in further detail below, fastening elements 712 can be integrally formed with their underlying substrate, in this case flap 704. For example, fastening elements and their underlying substrate can be formed from a single mass of resin.

Figure 22:
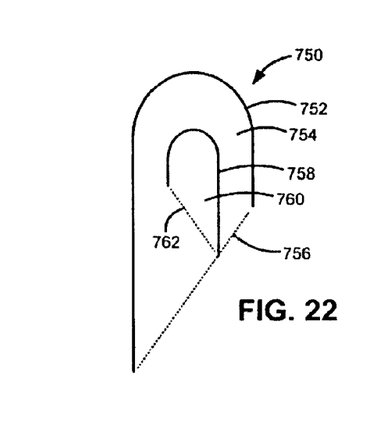
FIG. 22 is a plan view of an exemplar embodiment of a fastening strip in accordance with the present disclosure.

With particular reference to FIG. 22, an exemplar flap arrangement 750 is illustrated. Flap arrangement 750 includes an outer, arcuate slit 752 that defines an outer, arcuate flap 754. Outer flap 754 can fold along an axis 756. Flap arrangement 750 further includes an inner, arcuate slit 758 that defines an inner, arcuate flap 760. Inner flap 760 can fold along an axis 762 that is non-parallel to axis 756. Consequently, outer flap 754, and inner flap 760 fold in different directions. When implemented with a fastening strip, such as those described herein, flap arrangement 750 can compound the shear force required to disengage mating fastening strips as the fastening strips are pulled apart.

Figure 23A:
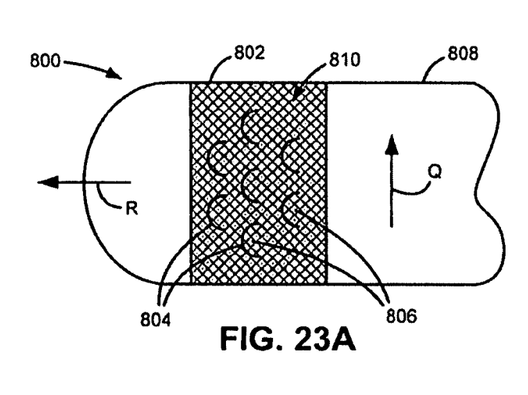
FIG. 23A is a plan view of a fastening tab including a fastening strip in accordance with the present disclosure.
Figure 23B:
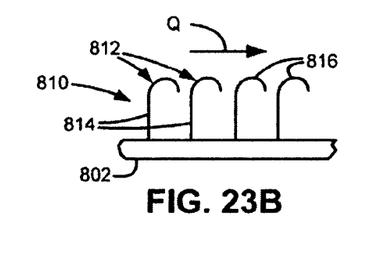
FIG. 23B is a schematic side view of exemplar hook fasteners.

Referring now to FIGS. 23A and 23B, an exemplar tab 800 is illustrated that includes a fastening strip 802 in accordance with the present disclosure. Exemplar tab 800 can be implemented in any number of products including, but not limited to, clothing, shoes, and/or personal care garments, such as diapers. Fastening strip 802 includes a plurality of slits 804 that define flaps 806, and is attached to a tab body 808. Although slits 804, and therefore flaps 806, are semi-circular in shape, the slits and flaps can include any one of a plurality of shapes, as discussed in detail above. Further, although fastening strip 802 includes three rows of slits 804/flaps 806 that are misaligned with one another, any other arrangement, alignment, or misalignment of slits 804/flaps 806 is within the scope of the present disclosure.

With particular reference to FIG. 23B, the fastening strip 802 includes a field 810 of J-hook and/or palm tree type fastening elements 812. More specifically, each fastening element 812 includes a stem portion 814 and a crook portion 816. Crook portions 816 open in the direction indicated by arrow Q. Fastening elements 812 of the field 810 run across a width of tab body 808 in the direction indicated by arrow Q. Consequently, fastening elements 812 run in a direction that is at or near perpendicular to an opening direction of tab 800, which is indicated by an arrow R. Because fastening elements 812 are aligned at or near perpendicular to the opening direction of tab 800, the holding strength of J-hook fastening elements 812, and corresponding loop fastening elements (not shown) is enhanced. As discussed in further detail below, fastening elements 812 can be integrally formed with fastening strip 802. For example, fastening elements and their underlying substrate can be formed from a single mass of resin.

Figure 24:
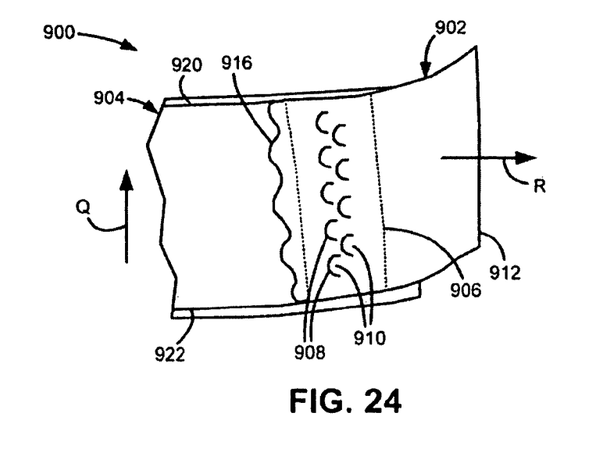
FIG. 24 is a perspective view illustrating a release progression of a fastening tab including a fastening strip in accordance with the present disclosure.

Referring now to FIG. 24, an exemplar tab arrangement 900 that includes an exemplar tab 902, and a mating tab 904 will be described. Exemplar tab arrangement 900 can be implemented in any number of products including, but not limited to, clothing, shoes, and/or personal care products, such as diapers. Tab 902 includes a fastening strip 906 in accordance with the present disclosure. Fastening strip 906 includes a plurality of slits 908 that define flaps 910, and is attached to a tab body 912. Although slits 908, and therefore flaps 910, are arcuate in shape, in this case semi-circular, the slits and flaps can include any one of a plurality of shapes, as discussed in detail above. Further, although fastening strip 906 includes two rows of slits 908/flaps 910 that are misaligned with one another, any other arrangement, alignment, or misalignment of slits 908/flaps 910 is within the scope of the present disclosure. Tab body 912 further includes a pull edge 916 that provides a non-fastening, grip area that can be pulled to initiate disengagement of tabs 902, 904.

Fastening strip 906 can include hook-type fastening elements, or loop-type fastening elements. Similarly, fastening strip 920 can include hook-type fastening elements, or loop-type fastening elements. More specifically, if fastening strip 906 includes hook-type fastening elements, then fastening strip 920 includes mating loop-type fastening elements. On the other hand, if fastening strip 906 includes loop-type fastening elements, then fastening strip 920 includes mating hook-type fastening elements. As tab 902 is pulled from engagement with tab 904 in the direction indicated by the arrow R flaps 910 initially disengage from fastening strip 920 requiring a peel force and an added shear force to be applied. In this manner, accidental disengagement of tabs 902, 904 can be inhibited. For example, if pull edge 916 accidentally catches on an object, complete disengagement of tabs 902, 904 can be inhibited by the added shear force that would be required as a result of the engagement of flaps 910.

In another embodiment of tab arrangement 900, the hook-type fastening elements can be arranged to be aligned in across a width of the respective tab body 912, 922 in the direction indicated by arrow Q, regardless of which fastening strip 906, 920 includes hook-type fastening elements. Consequently, the hook-type fastening elements run in a direction that is at or near perpendicular to an opening direction of tab 902, which is indicated by an arrow R. This is similarly described above with respect to FIG. 23A. Because the hook-type fastening elements are aligned at or near perpendicular to the opening direction of tab 902, the holding strength of the hook-type fastening elements, and the mating loop-type fastening elements is enhanced.

Figure 25A:
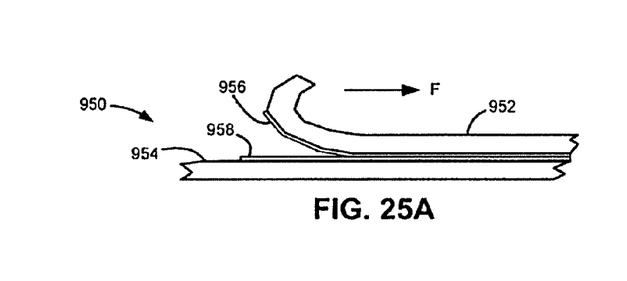
FIGS. 25A-25C illustrate exemplar fastening strips and corresponding force profiles.
Figures 25B, 25C:
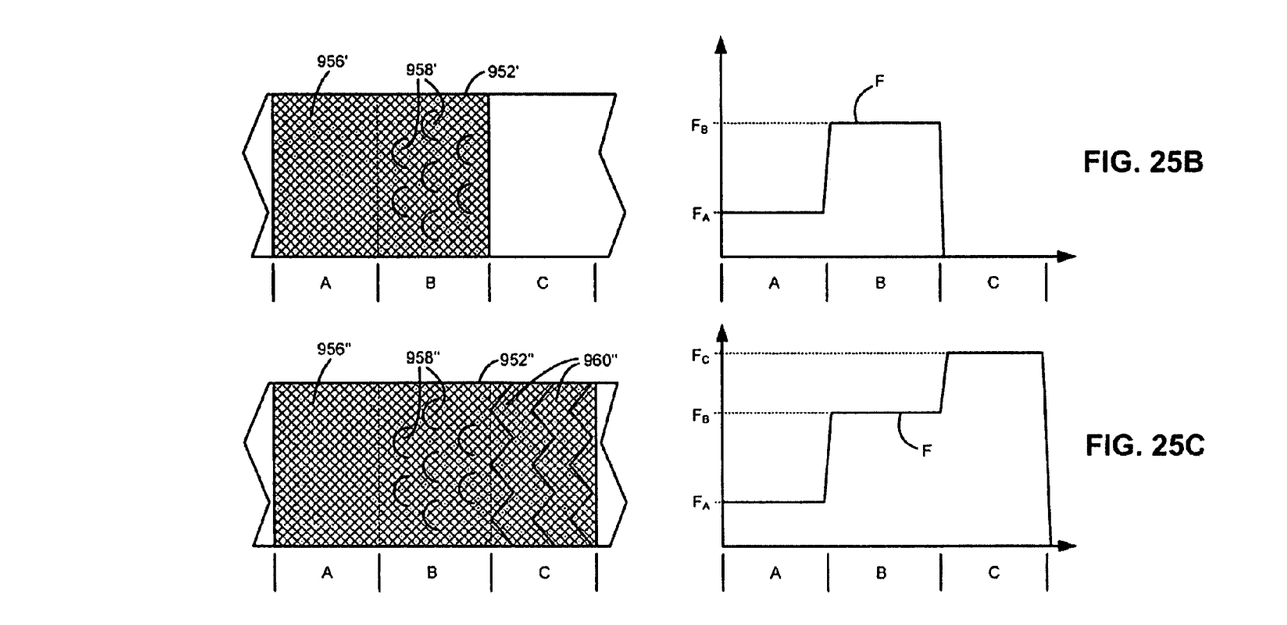

Referring now to FIGS. 25A-25C, exemplar force profiles for disengaging exemplar fastening strips will be described. With particular reference to FIG. 25A, an exemplar fastening arrangement 950 includes a first fastening 952, and a mating, second fastening 954. First fastening 952 is releasably secured to second fastening 954, whereby a fastening strip 956 that is fixed to first fastening 952 releasably engages a fastening strip 958 that is fixed to second fastening 954. More specifically, a force F can be applied to first fastening strip 952 to peel first fastening strip 952 from engagement with second fastening strip 954, releasing fastening strip 956 from fastening strip 958.

With particular reference to FIG. 25B, a fastening 952' includes a fastening strip 956' that includes fastening elements. The fastening elements can include either hook-type fastening elements, or loop-type fastening elements. Fastening strip 956' can be divided into regions A, B, and C. Region A, for example, can be a traditional fastening element arrangement. Region B, however, includes a plurality of flaps 958'. Although flaps 958' are arcuate in shape, in this case semi-circular, flaps 958' can include any one of a plurality of shapes, as discussed in detail above. Further, although three misaligned rows of flaps 958' are illustrated, any other arrangement, alignment, or misalignment is within the scope of the present disclosure.

As fastening 952' is pulled from engagement with a mating fastening, such as fastening 954 of FIG. 25A, a variable amount of force is required. More specifically, a first force $F_A$ is required to disengage region A of fastening strip 956' from a mating fastening strip, as illustrated in the force profile of FIG. 25B. First force $F_A$ is substantially a pull, or peel force. As disengagement of the fastenings progresses to region B, a second force $F_B$ is required. Second force $F_B$ is greater than first force $F_A$, and includes both a peel force and an added shear force. The added shear force is the force required to release flaps 958' from engagement in a shear direction. Fastening strip 956' ends at the end of region B. Accordingly, no force is required thereafter.

With particular reference to FIG. 25C, a fastening 952" includes a fastening strip 956" that includes fastening elements. The fastening elements can include either hook-type fastening elements, or loop-type fastening elements. Fastening strip 956" can be divided into regions A, B, and C. Region A, for example, can be a traditional fastening element arrangement. Region B, however, includes plurality of flaps 958". Although flaps 958" are arcuate in shape, in this case semi-circular, flaps 958" can include any one of a plurality of shapes, as discussed in detail above. Further, although three misaligned rows of flaps 958" are illustrated, any other arrangement, alignment, or misalignment is within the scope of the present disclosure. Region C includes flaps 960" that extend across the width of fastening strip 956". Although flaps 956" are provided in three rows and include a sharp, zig-zag shape, other arrangements of flaps 956" are anticipated within the scope of the present disclosure.

As fastening 952" is pulled from engagement with a mating fastening, such as fastening 954 of FIG. 25A, a variable amount of force is required. More specifically, a first force $F_A$ is required to disengage region A of fastening strip 956" from a mating fastening strip, as illustrated in the force profile of FIG. 25C. First force $F_A$ is substantially a pull, or peel force. As disengagement of the fastenings progresses to region B, a second force $F_B$ is required. Second force $F_B$ is greater than first force $F_A$, and includes both a peel force and an added shear force. The added shear force is the force required to release flaps 958" from engagement in a shear direction. As disengagement of the fastenings progresses to region C, a third force $F_C$ is required. Third force $F_C$ is greater than second force $F_B$, and is substantially a shear force. The shear force is the force required to release flaps 960" from engagement in a shear direction. Fastening strip 956" ends at the end of region C. Accordingly, no force is required thereafter.

Although hook and loop type, touch fastener arrangements have been described herein, it is anticipated that the principles of the present disclosure can be implemented with other fastening arrangements. Exemplar other fastening arrangements can include, but are not limited to, self-engaging fasteners, such as hook-hook type fasteners, gecko-type nano fasteners, suction-cup type fasteners, and/or adhesive fasteners. In the case of an adhesive fastener, the fastening arrangement can include a substrate that carries an adhesive on a surface thereof. The adhesive can be carried on the entire surface and/or surfaces associated with flaps formed through the substrate. Self-engaging fasteners can include two fastening members, each of which includes fastening elements. On the other hand, gecko-type nano fasteners, suction-cup type fasteners, and/or adhesive fasteners can have two fastening members, where only one of the fastening members includes fastening elements. For example, a first fastening member can include a strip, or tape that has fastening elements on a surface thereof, which fastening elements engage a corresponding surface of a second fastening member. The second fastening member can include a strip, or tape, and/or any object, to which the first fastening member is to be attached. The corresponding surface of the second fastening member need not include it's own fastening elements. The cuts and flaps of the present disclosure can be implemented in the first fastening member, for example, to improve the engagement strength between the first and second fastening members.

The fastening members of the present disclosure can be manufactured in various manners. An exemplar manufacturing process is described in commonly assigned U.S. Pat. No. 4,794,028 to Fischer, the entire disclosure of which is expressly incorporated herein by reference. In short, an extrusion of plastic material is shaped between a pair of co-acting first and second rollers. One of the rollers defines a plurality of hook-forming cavities about its periphery, within which the hook projections of the fastener member are formed. Another exemplar manufacturing process is described in U.S. Patent Application Publication No. US 2005/0079321, the entire disclosure of which is also incorporated herein by reference. In short, a precursor film, or strip having a series of hook-shaped ribs is formed. The series of ribs are transversely cut at spaced locations, and the strip is stretched to displace resultant hook projections relative to one another. The above-described manufacturing processes are merely exemplar in nature, and any manufacturing process can be implemented in conjunction with the present disclosure.

Figure 26:
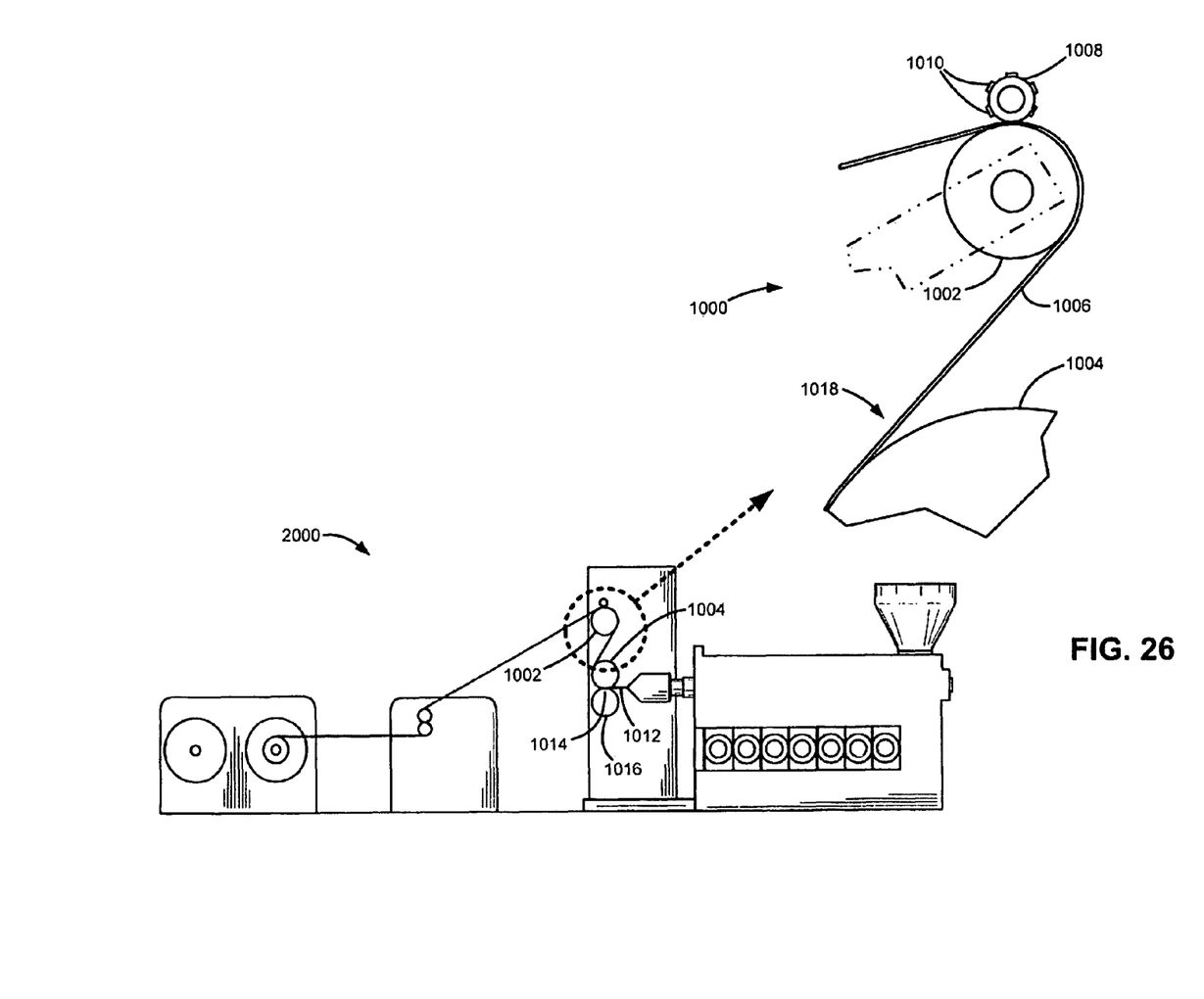
FIG. 26 illustrates a portion of a manufacturing arrangement.

In general, a sheet-form base and fastening elements that extend from a broad surface of the base can be formed from a resin. Slits can be formed to define flaps of the base connected only along an adjoining edge but otherwise flexible out of a plane of the base, each flap carrying at least one of the fastening elements. The slits can be formed in various manners. In one embodiment, the slits can be formed using a punch. With particular reference to FIG. 26, a portion of a manufacturing arrangement 1000 having rollers 1002, 1004 is illustrated. The fastening member can be provided as a continuous strip 1006, and the punch can be provided as a rotary punch 1008, having punch forms 1010 extending therefrom. Although fastening elements are not illustrated on continuous strip 1006, it is appreciated that fastening elements can be formed on continuous strip 1006 prior to forming the slits. Forming of the slits can occur in a rotary cutting operation, where continuous strip 1006 passes between roller 1002 and rotary punch 1008, which punches the slits into continuous strip 1006 as it passes thereunder. Subsequently, continuous strip 1006 can be provided to an end-user as a roll, or can be cut into individual strip sections. Manufacturing arrangement 1000 can be similar to that described in U.S. Pat. No. 4,794, 028, where roller 1004 includes a pressure, or mold roller that can be implemented to form hook-type fastening members.

As illustrated in FIG. 26, manufacturing arrangement 1000 can be implemented with a molding system 2000 that uses mold roller 1004 for the production of fastener elements for touch fastener products. The process and basic machine shown are in accordance with the techniques as described in U.S. Pat. Nos. 4,775,310, 4,794,028, 4,872,243, and 6,258, 311, the entire disclosures of which are incorporated herein by reference. The mold roller 1004 has miniature fastener shaped mold cavities about its periphery for forming fastener projections on an extruded strip-form touch fastener product that is provided as continuous strip 1006. Mold roller 1004 can include many annular, thin mold plates of, for instance, 10 to 12 inch diameter, held together as a stack. Heat-softened synthetic resin 1012 is forced into the cavities under pressure at nip 1014, between mold roller 1004 and a pressure roller 1016. In a continuous process, the fastener projections at least partially solidify in the mold cavities, and are then pulled out of the cavities in area 1018 after the product has cooled to a temperature at which the projections have solidified sufficiently to be pulled intact out of their mold cavities, remaining integral with the base sheet of the product. The projections are pulled out of mold roller 1004 by passing the product around roller 1002.

The various embodiments of the fastening arrangements described herein improve the engagement strength of mating fastening members. Consequently, lighter weight, and/or a reduced amount of fastening elements can be implemented. More specifically, the engagement strength of fastening members is decreased when using lighter weight, and/or a reduced amount of fastening elements. The increased engagement strength associated with the fastening arrangements of the present disclosure can offset any decrease in engagement strength that may result when using lighter weight, and/or a reduced amount of fastening elements. Furthermore, the fastening arrangements described herein, inhibit accidental disengagement of fastening members. This can be particularly beneficial in the case of implementation with a personal care garment, such as a diaper.

A number of embodiments of the present disclosure have been described. Nevertheless, it will be understood that various modifications may be made without departing from the spirit and scope of the present disclosure. Accordingly, other embodiments are within the scope of the following claims.

What is claimed is:

1. A releasable fastening arrangement, comprising:
   a first fastening strip secured to and extending over a substrate surface and having a first surface carrying first fastening elements extending from the first surface; and
   a second fastening strip having a second surface carrying second fastening elements that are engageable by the first fastening elements to form a releasable fastening;
   wherein the first surface includes a flexible flap that is formed therein, and that is surrounded by other portions of the first surface, the flap carrying at least one of the first fastening elements, the flap having a distal edge that is displaceable from the substrate surface under peel loads applied to the at least one first fastening element carried by the flap.

2. The releasable fastening arrangement of claim 1, wherein the flap is defined by a slit extending through the first fastener strip, such that the flap comprises a portion of the first surface extending from a remainder of the first surface only along one side of the flap opposite the distal edge.

3. The releasable fastening arrangement of claim 2, wherein the slit is curved.

4. The releasable fastening arrangement of claim 1, wherein the flap is arcuate and is flexible along a slanted axis.

5. The releasable fastening arrangement of claim 1, wherein the flap extends across a width of the first fastening strip.

6. The releasable fastening arrangement of claim 1, further comprising a second flap that is formed in the first surface, and that is surrounded by other portions of the first surface, the second flap carrying at least one of the first fastening elements, the second flap having a distal edge that is displaceable from the substrate surface under peel loads applied thereto, and extending across a width of the first fastening strip.

7. The releasable fastening arrangement of claim 1, wherein the first fastening strip includes multiple, spaced apart flaps, each carrying a respective one or more first fastening elements and each surrounded by non-flap portions of the first fastening product.

8. The releasable fastening arrangement of claim 1, wherein the first fastening elements and the first surface are of a single, seamless mass of resin.

9. The releasable fastening arrangement of claim 1, wherein the second fastening elements are provided as a field of fibers that are releasably engageable by the first fastening elements.

10. The releasable fastening arrangement of claim 1, wherein the first fastening strip is secured to the substrate surface in a region directly surrounding the flap.

11. A product comprising:
    a first fastening strip secured to and extending over a substrate surface of a first component of the product, the first fastening strip having a first surface carrying first fastening elements extending from the surface; and
    a second fastening strip secured to and extending over a substrate surface of a second component of the product, the second fastening strip having a second surface carrying second fastening elements that are engageable by the first fastening elements to form a releasable fastening;
    wherein the first surface includes a flexible flap that is formed therein, and that is surrounded by other portions of the first surface, the flap carrying at least one of the first fastening elements, the flap having a distal edge that is displaceable from the substrate surface of the first component of the product under peel loads applied to the at least one first fastening element carried by the flap.

12. The product of claim 11, wherein the flap is defined by a slit extending through the first fastener strip, such that the flap comprises a portion of the first surface extending from a remainder of the first surface only along one side of the flap opposite the distal edge.

13. The product of claim 12, wherein the slit is curved.

14. The product of claim 11 wherein the flap is arcuate and is flexible along a slanted axis.

15. The product of claim 11, further comprising a second flap that is formed in the first surface, and that is surrounded by other portions of the first surface, the second flap carrying at least one of the first fastening elements, the second flap having a distal edge that is displaceable from the substrate surface under peel loads applied thereto, and extending across a width of the first fastening strip.

16. The product of claim 11, wherein the first fastening strip includes multiple, spaced apart flaps, each carrying a respective one or more first fastening elements and each surrounded by non-flap portions of the first fastening product.

17. The product of claim 11, wherein the first fastening elements and the first surface are of a single, seamless mass of resin.

18. A releasable fastener product, comprising:
    a flexible sheet-form base having an exposed surface; and
    a field of fastener elements extending from the surface;
    wherein the base is slit to define flaps that have a distal edge and that are connected only along an adjoining edge, but are otherwise flexible out of a plane of the base, each flap carrying at least one of the fastener elements of the field.

19. The fastener product of claim 18, wherein each flap is defined by a slit extending through the flexible sheet form, such that the flap comprises a portion of the surface extending from a remainder of the surface only along one side of the flap opposite the distal edge.

20. The fastener product of claim 18, wherein each flap extends across a width of the base.

* * * * *